(12) United States Patent
Stanbridge et al.

(10) Patent No.: US 6,245,509 B1
(45) Date of Patent: *Jun. 12, 2001

(54) DETECTION OF MICROORGANISM BY DNA HYBRIDIZATION

(75) Inventors: Eric J. Stanbridge, Corona del Mar, CA (US); Ulf B. Gobel, Berlin (DE)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/152,375

(22) Filed: Sep. 14, 1998

Related U.S. Application Data

(63) Continuation of application No. 08/469,600, filed on Jun. 6, 1995, now Pat. No. 5,851,767, which is a continuation of application No. 08/136,723, filed on Oct. 14, 1993, now abandoned, which is a continuation of application No. 08/020,874, filed on Feb. 19, 1993, now abandoned, which is a continuation of application No. 07/799,856, filed on Nov. 27, 1991, now abandoned, which is a continuation of application No. 07/191,852, filed on May 6, 1988, now abandoned, which is a continuation of application No. 06/707,725, filed on Mar. 4, 1985, now abandoned.

(51) Int. Cl.[7] .............................. C12Q 1/08; C12N 15/11; C07H 21/04
(52) U.S. Cl. ............................ 435/6; 435/91.1; 435/91.5; 536/23.1; 536/24.3; 536/24.31; 536/24.32
(58) Field of Search ......................... 435/6, 91.1, 91.5; 536/23.1, 24.3, 24.31, 24.32

(56) References Cited

U.S. PATENT DOCUMENTS

| | | | |
|---|---|---|---|
| 5,132,207 | 7/1992 | Kohne | 435/6 |
| 5,567,587 | 10/1996 | Kohne | 435/6 |
| 5,601,984 | 2/1997 | Kohne | 435/6 |
| 5,612,183 | 3/1997 | Kohne | 435/6 |
| 5,641,631 | 6/1997 | Kohne | 435/6 |
| 5,641,632 | 6/1997 | Kohne | 435/6 |
| 5,688,645 | 11/1997 | Kohne | 435/6 |
| 5,714,324 | 2/1998 | Kohne | 435/6 |
| 5,723,597 | 3/1998 | Kohne | 536/24.3 |
| 5,738,988 | 4/1998 | Kohne | 435/6 |
| 5,738,989 | 4/1998 | Kohne | 435/6 |
| 5,851,767 | * 12/1998 | Stanbridge et al. | 435/6 |

FOREIGN PATENT DOCUMENTS

0124221 A1 3/1983 (EP).
0127327 A1 4/1983 (EP).

OTHER PUBLICATIONS

Nucleotide Sequence Homology Between the Heat–Labile Enterotoxin Gene of *Escerichia coli* and *Vibrio cholerae* Deoxyribonucleic Acid, Journal of Bacteriolody, Oct. 1980 p444–446, Mosley et al.

Nucleotide sequence of the rrnB 16S ribosomal RNA gene from *Mycoplasma capricolum*, Molecular Genetics, 1984; 196(2):317–22, Furo–Cho et al.

Comparative Analysis of Mycoplasma Ribosmal RNA Operons, Israel Journal of Medical Sciences, vol. 20, 1984, p.762–763 U. Göbel et al.

Hybridization of Nucleic Acids Immobilized on Solid Supports, Analytical Biochemistry 138, 1984 pp267–284 Meinkoth et al.

Synthesis and Conformational Analysis of Synthetic DNA Fragments, Cold Spring Harbor Symp. Quant Biol. 1983, pp. 403–409, J.H.vanBoom et al.

Hybridization With Synthetic Oligonucleotides, Methods in Enzymology, vol. 68 pp 419–428, 1979, Szostak et al.

Detection of Enterotoxigenic *Escherichia coli* by DNA Colony Hybridization, Journal of Infectious Diseases, vol. 142 No. 6, 1980, pp. 892–898 Moseley et al.

DNA Hybridization Technique for the Detection of *Neisseria gonorrhoeaa* in Men with Urethritis, Journal of Infectious Diseases, vol. 148, No. 3, 1983 Totten et al.

Nucleotide Sequence Homology Between the Immunoglobulin A1 Protease Genes of *Neisseria gonorrhoeae*, *Neisseria meningitidis*, and *Haemophilus influenzae* Infection and Immunity 1984, pp 101–107 Koomey et al.

Hybridization of synthetic oligodeoxyribonucleotides to Φχ 174 DNA: the effect of single base pair mismatch, Nucleic Acids Research, vol. 6 No. 11, 1979, pp 3543–3557, Wallace et al.

The use of synthetic oligonucleotides as hybridization probes. II. Hybridization of oligonucleotides of mixed sequence of rabbit –globin DNA, Nucleic Acids Research, vol. 9, No. 4, 1981, pp. 879–894, Wallace et al.

Primary Sequence of the M.pneumoniae 16S—rRNA published as an Abstract for the Annual Meeting of the American Society for Microbiology in Mar. 1985, by Andrew Geiser, Ulf B. Gobel, Gary Butler and Eric J. Standbridge.

A Mycoplasma–Specific Olegonucleotide Probe Derived from the 16S—rRNA Gene, by Ulf B. Gobel, David A. Smith and Eric J. Stanbridge.

* cited by examiner

*Primary Examiner*—David Guzo
(74) *Attorney, Agent, or Firm*—Fulbright & Jaworski L.L.P

(57) ABSTRACT

Biological probes useful for detecting mycoplasmas or prokaryotes in general, or specific mycoplasma and eubacterial species are derived from the ribosomal RNA gene by selecting particular nucleotide sequences common to the class of organisms being detected.

4 Claims, 1 Drawing Sheet

DETECTION OF MICROORGANISM BY DNA HYBRIDIZATION

Cross-Reference to Related Applications

This application is a continuation of application Ser. No. 08/469,600 filed Jun. 6, 1995, now U.S. Pat. No. 5,851,767 which is a continuation of application Ser. No. 08/136,723 filed Oct. 14, 1993 now abandoned, which is a continuation of application Ser. No. 08/020,874 filed Feb. 19, 1993 now abandoned, which is a continuation of application Ser. No. 07/799,856 filed Nov. 27, 1991 now abandoned, which is a continuation of application Ser. No. 07/191,852 filed May 6, 1988 now abandoned, which is a continuation of application Ser. No. 06/707,725 filed Mar. 4, 1985.

Regarding Federally Sponsored Research or Development

This invention was made with Government support under Grant No. AI/AM 14096-01 with the National Institutes of Health and the University of California. The Government has certain rights in this invention.

FIELD OF THE INVENTION

This invention relates generally to the field of Biology, and more particularly to the fields of Biomedicine, Biochemistry and Molecular Biology.

BACKGROUND AND SUMMARY OF THE INVENTION

Mycoplasmas are a group of pathogenic microorganisms of the Class Mollicutes characterized by having a small size and lacking a cell wall. These microorganisms are among the smallest-known organisms capable of a free living existence, and are important pathogens in man, plants and animals. For example, atypical pneumonia and non-gonococcal urethritis are common mycoplasma infections in man. Mycoplasmas have also been associated with rheumatoid arthritis, spontaneous abortion, infertility and other genital tract diseases, and certain autoimmune disease states. Moreover, mycoplasmas are common contaminants in cell cultures. In biological research, mycoplasma contamination of tissue culture is a serious problem which demands constant monitoring.

Not surprisingly, these organisms are extremely fastidious and at present there are no cost-effective specific diagnostic procedures to determine the presence of mycoplasma infections. The most commonly employed detection methods for mycoplasmas in clinical samples are serological and cultural. The serological methods are subject to false positives and the cultural methods are costly, time consuming and tedious. Many of the biochemical techniques in current usage for detection of microbial contaminants in cell cultures do not specifically detect mycoplasmas but rather indicate the presence of any prokaryote or simple eukaryote such as yeast and fungi, and some may even detect viruses. Such a test is advantageous if one is interested only in the knowledge that a microbial agent is present, but if one is searching for a suspected etiological agent of an animal or human disease it is obviously necessary to classify the agent as fully as possible.

Further, the above procedures are hampered by special problems. For example, there are apparently "non-cultivable" mycoplasmas which are not detected by conventional culture methods. In addition, in the case of immunofluorescence tests more than one antibody might be required to identify the particular organism since more than nine different mycoplasma species are common tissue culture contaminants. Also, DNA stains are not necessarily mycoplasma-specific.

Therefore, a simple, sensitive, specific, cost-effective, and rapid mycoplasma detection system has been a desideratum in the fields of diagnostic medicine and biological research.

The use of nucleotide sequence homology and nucleic acid hybridization kinetics has become a widely-employed technique for detecting various organisms in cells and cell cultures. However, prior to this invention reliable and specific DNA probes have not been available for mycoplasma detection.

The present invention proceeds by the use of specific mycoplasma ribosomal RNA gene fragments which are labeled or tagged by a variety of techniques, such as radioisotope labeling, biotin labeling, PEI-peroxidase conjugates, or fluorescent antibody tagging ELISA methods, for the specific and sensitive detection of mycoplasmas in clinical specimens, cells or cell cultures by DNA or RNA hybridization.

In one aspect of the invention, a DNA sequence from the 16S RNA gene of mycoplasma is provided, which includes a nucleotide sequence selected from the group consisting of AACACGTATC, CGAATCAGCTATGTCG, GAGGTT----AAC, ATCCGGATTTATT, TCTCAGTTCGGATTGA, AGGTGGTGCATGGTTG, TCCTGGCTCAGGAT, ATACATAGGT, MCTATGTGC, AATTTTTCACAATG, TCTCGGGTCT, and TAGATATATG which code for mycoplasma ribosomal RNA (rRNA) where T represents thymine, G represent guanine, A represents adenine, C represents cytosine and—indicates a nucleotide deletion within the sequence with respect to the comparable sequence in E. coli. These fragments differ significantly from the 16S RNA gene of E. coli, and thus form the basis for mycoplasma-specific probes which are constituted of labeled nucleotide sequences complementary to the above.

In another aspect of the invention, identified DNA sequences of a 16S RNA gene are provided which include nucleotide sequences selected from the group consisting of ACGGGTGAGT, TMTACCGCAT, TACGGGAGGCAGCAGT, GTGGGGAGCAAA, AGGATTAGATACCCT, CCGTAAACGAT, GAATTGACGGGG, CCCGCACAAG, GGTGGAGCATGT, TGTTGGGTTAAGTCCCGCAACGA, GGGATGACGT, ACGTGCTACAATG, CTAGTAATCG, TGTACACACCGCCCGTCA, AAGTCGTAACAAGGTA, and TGGATCACCTCCTT, which code for prokaryotic rRNA. These fragments represent regions within the 16S RNA gene that are identical for E. coli and all mycoplasmas examined. Universal probes for all prokaryotes are constituted of labeled nucleotide sequences complementary to these fragments.

In general the invention comprises a method for determining the presence of a prokaryotic organism which contains a nucleic acid including a particular nucleotide sequence which is present in nucleic acids from prokaryotic organisms but absent in nucleic acids from eukaryotic organisms, which comprises contacting a medium which may contain a nucleic acid or nucleic acid fragment from said prokaryotic organism including said particular nucleotide sequence with an oligonucleotide, including a nucleotide sequence complementary to said particular nucleotide sequence, whereby said oligonucleotide hybridizes with any nucleic acid or nucleic acid fragment from said prokaryotic organism, including said particular nucleotide sequence which may be present in said medium, and detecting the presence of any nucleic acid or nucleic acid fragment hybridized with said oligonucleotide.

Other aspects of the invention concern the specific biological probes used for detecting mycoplasmas or prokaryotes in general in accordance with the above described process and the identification and production of such probes.

DESCRIPTION OF THE PREFERRED EMBODIMENTS

Figure 1:
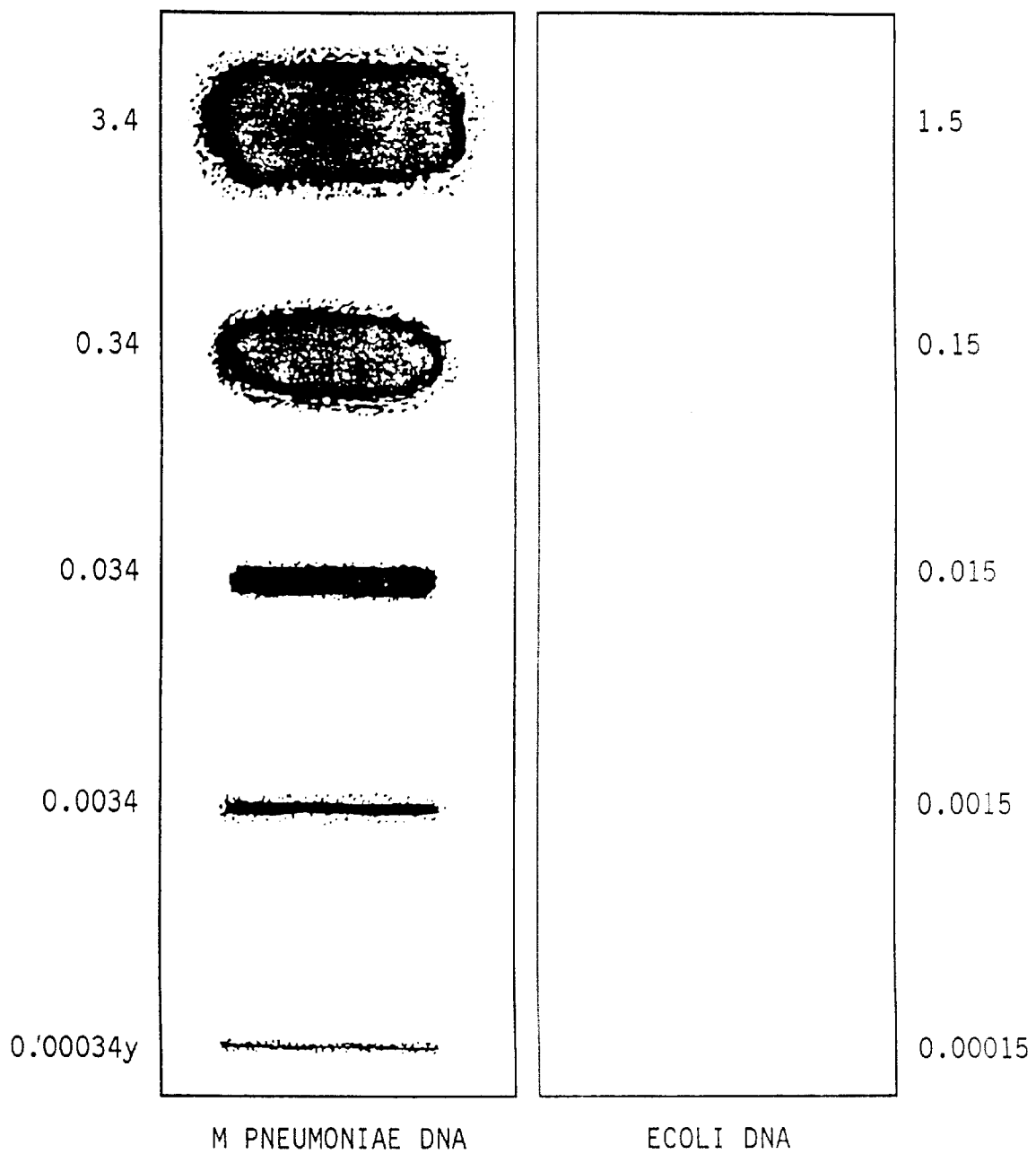
FIG. 1. The sole FIGURE of the drawing shows a slot blot development illustrating the present invention.

The invention will now be described by detailing first the specific steps involved in producing and using the biological probes of the present invention and then describing how particular nucleotide sequences useful in this invention are determined.

SYNTHESIS OF DEOXYOLIGONUCLEOTIDES

The 16bp deoxyoligonucleotide, GCTTAGTCGATACAGC, which is complementary to one of the 16S mycoplasma RNA gene sequences listed above, was synthesized using the phosphotriester solid phase procedure described in M. H. Caruthers et al., *Genetic Engineering* Vol.4, p.1–17, Plenum Publishing Co. (1982), which is hereby incorporated by reference and which discusses the synthesis and isolation of dioxyoligonucleotides.

Any of the other deoxyoligonucleotides previously mentioned or any other desired oligonucleotide can be similarly prepared. For example, instead of a DNA probe it may be desired to synthesize an RNA probe such as a recombinant SP6 vector transcript containing the sequence CGAAUCAGCUAUGUCG.

DNA-RNA or RNA-RNA hybridization to ribosomal RNA molecules amplifies the sensitivity of the detection several hundredfold above any DNA-DNA or RNA-DNA hybridization using probes against genomic DNA sequences, since the use of such probe will detect multiple copies of ribosomal RNA per mycoplasma or eubacterial cell.

TESTING OF DEOXYOLIGONUCLEOTIDES

The above described deoxyoligonucleotide was $^{32}$P-labeled at the 5' end using the procedure in C. C. Richardson, *Procedures in Nucleic Acid Research* (Cantoni, G. L. and Davies, D. R., eds.), Vol. 2, pp. 815–828, Harper and Row, New York (1971), which is hereby incorporated by reference. The resulting labeled deoxyoligonucleotide was then used as a mycoplasma-specific probe. Specificity for mycoplasma was demonstrated by means of slot blot hybridization as described in M. Cunningham, *Anal. Biochem.* 128:415–421 (1983), which is herein incorporated by reference. For this purpose a 1600 bp DNA fragment of Mycoplasma pneumoniae which had been cloned into pUC8 was used. The 1600 bp fragment contains the above described 16 base deoxyoligonucleotide. A genomic digest of *E. coli*, a representative prokaryotic eubacterium, was also produced by digestion with the enzyme HindIII. The digested *E. coli* DNA and the 1600 bp *M. pneumoniae* DNA fragment were transferred onto nitrocellulose filters according to the procedure in the J. J. Leary et al., *Proc. Natl. Acad. Sci. U.S.A.* 80:4045–4049 (1983), which is hereby incorporated by reference. The nitrocellulose filters containing the DNA fragments were baked for 2 hours at 80° C. under reduced pressure and hybridized to the $^{32}$P-labeled deoxyoligonucleotide. Development of the resulting slot blots, shown in the drawing, revealed blots of increasing intensity for the *M. pneumoniae* DNA segment at 0.00034 ng, 0.0034 ng, 0.034 ng, 0.34 ng, and 3.4 ng (calculated for 16 bp) and no blots for the *E. coli* DNA segment at 0.00015 µg, 0.0015 µg, 0.015 µg, 0.15 µg, and 1.5 µg indicating the specificity of the deoxyoligonucleotide probe for mycoplasma. The deoxyoligonucleotide having the sequence GCTTAGTC-GATACAGC thus is useful as a mycoplasma-specific probe which hybridizes with mycoplasmal DNA but does not hybridize with DNA of other prokaryotic organisms. On the other hand, a deoxyoligonucleotide having the sequence TGCCCACTCA, for example, which is complementary to one of the prokaryotic coding gene sequences, is useful as a prokaryote-specific probe which hybridizes with prokaryotes but not with eukaryotes.

For the detection of mycoplasmas in infected cells the following procedure has been found effective. The cells are trypsinized using 1-2 T75 tissue culture flasks with Trypsin EDTA(0.05% trypsin, 0.04% EDTA in PBS) for 2 minutes at 37° C. The trypsinized cells are resuspended in 1–2 ml of growth medium and spotted in a quantity of 50–100 µl ($1 \times 10^5 – 1 \times 10^6$ cells) onto a nitrocellulose filter wetted with 10×SSC (1×SSC: 15 mM Na citrate, 150 mM NaCl, pH 7.4) using a Minifold II slot blot hybridization apparatus available from Schleicher and Schuell, Inc., Keene, N. H. The DNA samples applied to the slot blots are denatured with alkali (0.5 M NaOH, 1.5 M NaCl) for 5–10 minutes at room temperature and neutralized for 5–10 minutes at room temperature using 0.5 M Tris, pH 7.2 and 3.0 M NaCl. The filter is then washed with 2×SSC for five minutes at room temperature and baked in a vacuum oven for 2 hours at 80° C. The filter is prehybridized for 2 hours at 65° C. using a prehybridization buffer consisting of 0.5 mM EDTA, 5 mM Tris, pH 7.5, 5×Denhardt, and 100 µg/ml heat denatured herring sperm DNA. Hybridization, using the probes of this invention in a concentration measured as $1–2 \times 10^6$ cpm of $^{32}$P-labeled deoxyoligonucleotide, specific activity >$10^8$ cpm/µg in hybridization buffer consisting of 10 mM Tris, pH 7.5, 1 mM EDTA, 0.75 M NaCl, 1×Denhardt, 0.5% SDS, 10% dextran sulfate and 100 µg/ml heat denatured herring sperm DNA, is carried out at 65° C. for 16 hours. Following hybridization the filter is washed 2–4 hours at 65° C. with 2×SET, 0.2% SDS (1×SET:30 mM Tris, pH 8.0, 150 mM NaCl) and 1–2 hours at room temperature with 4 mM Tris base. The filter is then dried and exposed on X-ray film using 1 or 2 Dupont Cronex, intensifying screens.

DETERMINATION OF PARTICULAR NUCLEOTIDE SEQUENCES

While the foregoing description of the present invention teaches how particular nucleotide sequences can be prepared and used, the broader scope of this invention may be realized by examining the techniques used for determining particular nucleotide sequences which are useful as mycoplasma-specific probes, probes specific for prokaryotes in general, probes specific for individual mycoplasma, ureaplasma, acholeplasma, and spiroplasma species or probes specific for individual eubacterial species.

Such determination involves the following steps:

1. cloning the entire genome of ribosomal RNA of a particular species of mycoplasma into a bacteriophage or plasmid vector;

2. probing the resulting ribosomal RNA gene fragments with a non-mycoplasma prokaryotic ribosomal RNA operon;

3. characterizing the fragments which hybridize with said non-mycoplasma prokaryotic ribosomal RNA operon;

4. identifying mycoplasma-specific fragments by differential hybridization as described in Gobel, U. and Stanbridge, E. J., *Science,* Vol.226, pp.1211–1213 (1984), which is hereby incorporated by reference, and is described further below.

5. subcloning mycoplasma-specific fragments into a sequencing plasmid;

6. sequencing the resulting subcloned mycoplasma-specific fragments;

7. repeating steps 1–6 for other species of mycoplasma and for non-mycoplasmal prokaryotes; and 8. comparing sequences obtained in steps 6 and 7; whereby a sequence common to all the species of mycoplasma but differing from the corresponding sequence in non-mycoplasmal prokaryotes is useful as a mycoplasma-specific probe and a sequence common to all the species of mycoplasma, as well as the non-mycoplasmal prokaryotes, is useful as a probe specific for prokaryotes in general, and a sequence specific for either a specific mycoplasma, acholeplasma, ureaplasma, or spiroplasma species and sequences specific for any given eubacterial species, are useful as probes specific for individual mycoplasma, acholeplasma, ureaplasma, spiroplasma, or eubacterial species, respectively.

Cloning of the ribosomal RNA genome of *M. pneumoniae* was accomplished by HindIII digestion of total *M. pneumoniae* DNA and ligation of the HindIII fragments to the HindIII digested vector pUC8. The resulting ribosomal RNA gene fragments were probed with *E. coli* ribosomal RNA operon in the pKK 3535 plasmid according to the procedure in Gobel et al., *Science* 226:1211–1213 (1984), which is hereby incorporated by reference, to identify cloned fragments which contained ribosomal sequences.

There, we attempted to identify mycoplasmal DNA sequences that might account for these differences. A plasmid (pKK3535) that contains the entire rrnB operon of *E. coli* hybridized to six bands in Hind III--digested M. hyorhinis DNA. One of these bands, representing a 900-base-pair (bp) fragment from the 5'-terminal region of the M. hyorhinis 23S rRNA gene, disappeared when the hybridization was performed at higher temperatures, indicating a lower degree of homology between this particular fragment and the *E. coli* rrnB operon.

For further analysis, Hind III—digested M. hyorhinis DNA was cloned into the bacteriophage M13. Two clones, M13Mh129 and M13Mh171, contained inserts of 900 and 1200 bp in length, respectively, which hybridized to pKK3535. Mapping studies have shown that both fragments derive from the 23S rRNA gene (12). Both the 900- and 1200-bp fragments were purified and used as probes to identify rRNA gene (rDNA) fragments of representative Mycoplasnia species: M. arthritidis, M. fermentans, M. hominis, M. hyorhinis, *M. pneumoniae, and Acholeplasina laidlawii.*

We found comparable hybridization among all species tested. Since the 900-bp fragment showed less homology than the 1200-bp fragment to the *E. coli* rrnB operon we did the converse experiment by hybridizing the M13Mh129 fragment to Hind III -digested *E. coli* DNA. Hind III-digested HeLa-cell DNA was included in this experiment, to determine the extent of homology between Mycoplasma r DNA and eukaryotic genomic and mitochondrial rRNA genes. There was substantial cross-hybridization between the M. hyorhinis 900-bp probe and genomic DNA fragments of the two Mycoplasma species included in this experiment. The extent of cross-hybridization to *E. coli* was negligible and no cross-hybridization at all was found to HeLa DNA. In addition, purified nick-translated HeLa mitochondrial DNA did not hybridize to M. hyorhinis DNA digests transferred to nitrocellulose filters. The same result was found when nick-translated M13Mh129 was used to probe mitochondrial DNA restriction fragments immobilized on nitrocellulose filters.

Having demonstrated the specificity of the Mycoplasma rDNA probe, we adapted a dot-blot hybridization procedure for the detection of mycoplasma infection in tissue culture using the nick-translated 900-bp Hind III fragment of M13Mh129 as probe. The assay detected less than 0.5 pg of homologous DNA. This corresponds to the amount of rDNA contained in less than $1 \times 10_5$ mycoplasmas, assuming the presence of one rRNA operon in a genome of about 800 kilobase pairs (kbp) in size. We obtained similar values by blotting a suspension of mycoplasma-infected cells onto nitrocellulose filters. fewer than $1 \times 10_5$ mycoplasmas could be detected.

The results obtained with probe M13Mh129 show that it is specific for mycoplasmas and that the detection assay is quantitatively sensitive, ranking with the most sensitive indirect methods.

Here, a 1600 bp fragment was chosen on the basis of hybridization to mycoplasma species and not to *E. coli* or mammalian DNA under stringent hybridization conditions. This 1600 bp fragment was removed from the pUC8 vector by means of HindIII digestion and ligated to M13Mp8 DNA bacterial virus for sequencing using the Sanger dideoxy method described in Sanger et al., *Proc. Natl. Acad. Sci. U.S.A.,* 74:5463–5467 (1977), which is hereby incorporated by reference.

Comparison of the sequences of the mycoplasma species *M. pneumoniae, M. capricolum,* and *Mycoplasma species PG*50 with *E. coli* indicated that certain sequences were common to all these species of mycoplasma but different from *E. coli.* These sequences could be synthesized and labeled and used as mycoplasma--specific probes. For example, GCTTAGTCGATACAGC constituted a mycoplasma-specific probe. Other sequences were common to these species of mycoplasma as well as *E. coli.* These latter sequences could be synthesized, labeled, and used as probes specific for all prokaryotic species. Still other sequences were unique to a single mycoplasma species and could be synthesized, labeled, and used as mycoplasma species-specific probes.

The present invention thus provides a specific, sensitive, and rapid method for the detection of mycoplasmas in contaminated cell cultures or other biological environments. Alternatively, the present invention can be used to provide a ribosomal DNA probe derived from a domain conserved in all prokaryotes. Such a probe would be extremely useful in the rapid and sensitive diagnosis of a bacteremia or septicemia in man or animals. The present invention may also be used to provide ribosomal DNA probes that are specific for individual mycoplasma, acholeplasma, ureaplasma, spiroplasma, and eubacterial species, respectively. These probes will be of particular use for those organisms where little or no information exists on their genetic make-up.

Although the present invention has been described in detail by reference to certain specific examples of deoxyoligonucleotides and mycoplasma species, it should be apparent to one skilled in the art that various modifications are possible. It is intended that this invention include such modifications and that the invention be limited only in accordance with the claims appended hereto.

What is claimed is:

1. A method for obtaining an oligonucleotide probe that is hybridizable under predetermined conditions to a nucleotide sequence contained by one or more target organisms but not by one or more selected non-target organisms in a sample, wherein said target and non-target organisms are no higher phylogenetically than prokaryotes, the method comprising:

a) obtaining particular nucleotide sequence information of one or more of said target organisms;

b) obtaining particular nucleotide sequence information of one or more of said selected non-target organisms;

c) comparing said target and non-target sequence information and identifying therefrom at least one oligonucleotide sequence that is hybridizable under said predetermined conditions to a nucleotide sequence from said one or more target organisms but not to a nucleotide sequence from said one or more selected non-target organisms; and d) synthesizing and isolating an oligonucleotide comprising a sequence identical to said identified sequence.

2. A method for obtaining an oligonucleotide probe that is hybridizable under predetermined conditions to a nucleotide sequence contained by one or more target organisms but not by one or more selected non-target organisms in a sample wherein said target and non-target organisms do not have a cellular nucleus, the method, comprising:

a) obtaining particular nucleotide sequence information of one or more of said target organisms;

b) obtaining particular nucleotide sequence information of one or more of said selected non-target organisms;

c) comparing said target and non-target sequence information and identifying therefrom at least one oligonucleotide sequence that is hybridizable under said predetermined conditions to a nucleotide sequence from said one or more target organisms but not to a nucleotide sequence from said one or more selected non-target organisms; and d) synthesizing and isolating an oligonucleotide comprising a sequence identical to said identified sequence.

3. A method for obtaining an oligonucleotide probe that is hybridizable under predetermined conditions to a nucleotide sequence specific to one or more target organisms but not to one or more selected non-target organisms in a sample wherein said target and non-target organisms are no higher phylogenetically than prokaryotes, the method, comprising:

a) obtaining particular nucleotide sequence information of one or more of said target organisms;

b) obtaining particular nucleotide sequence information of one or more of said selected non-target organisms;

c) comparing said target and non-target sequence information and identifying therefrom at least one oligonucleotide sequence that is hybridizable under said predetermined conditions to a nucleotide sequence from said one or more target organisms but not to a nucleotide sequence from said one or more selected non-target organisms; and d) synthesizing and isolating an oligonucleotide comprising a sequence identical to said identified sequence.

4. A method for obtaining an oligonucleotide probe that is hybridizable under predetermined conditions to a nucleotide sequence specific to one or more target organisms but not to one or more selected non-target organisms in a sample, wherein said target and non-target organisms do not have a cellular nucleus, the method comprising:

a) obtaining particular nucleotide sequence information of one or more of said target organisms;

b) obtaining particular nucleotide sequence information of one or more of said selected non-target organisms;

c) comparing said target and non-target sequence information and identifying therefrom at least one oligonucleotide sequence that is hybridizable under said predetermined conditions to a nucleotide sequence from said one or more target organisms but not to a nucleotide sequence from said one or more selected non-target organisms; and d) synthesizing and isolating an oligonucleotide comprising a sequence identical to said identified sequence.

\* \* \* \* \*